US00PP23610P2

(12) United States Plant Patent
James

(10) Patent No.: US PP23,610 P2
(45) Date of Patent: May 21, 2013

(54) BIRCH TREE NAMED 'GLOBE'

(50) Latin Name: *Betula pendula*
Varietal Denomination: Globe

(75) Inventor: Colin James, Silvan (AU)

(73) Assignee: Kolster Holding B.V., Boskoop (NL)

( * ) Notice: Subject to any disclaimer, the term of this patent is extended or adjusted under 35 U.S.C. 154(b) by 0 days.

(21) Appl. No.: 13/373,734

(22) Filed: Nov. 28, 2011

(51) Int. Cl.
*A01H 5/00* (2006.01)

(52) U.S. Cl.
USPC ..... Plt./216

(58) Field of Classification Search ..... Plt./216
See application file for complete search history.

*Primary Examiner* — Kent L Bell
(74) *Attorney, Agent, or Firm* — C. A. Whealy

(57) ABSTRACT

A new and distinct cultivar of Birch tree named 'Globe', characterized by its dwarf habit; globular shape; freely branching habit, dense and bushy habit; glossy green-colored leaves; and no flower initiation or development.

2 Drawing Sheets

Botanical designation: *Betula pendula.*
Cultivar denomination: 'GLOBE'.

BACKGROUND OF THE INVENTION

The present invention relates to a new and distinct cultivar of Birch tree, botanically known as *Betula pendula*, commercially referred to as European White Birch and hereinafter referred to by the name 'Globe'.

The new Birch tree is a naturally-occurring branch mutation of *Betula pendula* 'Alba', not patented. The new Birch tree was discovered and selected by the Inventor from within a population of trees of 'Alba' in 1990 in an outdoor nursery in Melbourne, Australia.

Asexual reproduction of the new Birch tree by grafting since 1992 in a controlled outdoor nursery environment in Melbourne, Australia has shown that the unique features of this new Birch tree are stable and reproduced true to type in successive generations.

SUMMARY OF THE INVENTION

Trees of the new Birch have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Globe'. These characteristics in combination distinguish 'Globe' as a new and distinct Birch tree:

1. Dwarf habit.
2. Globular shape.
3. Freely branching habit, dense and bushy habit.
4. Glossy green-colored leaves.
5. No flower initiation or development.

Trees of the new Birch differ primarily from trees of the parent, 'Alba', in the following characteristics:

1. Trees of the new Birch are more dwarf than trees of 'Alba'.
2. Trees of the new Birch are bushier than trees of 'Alba'.

3. Trees of the new Birch do not produce flowers whereas trees of 'Alba' produce flowers.

Trees of the new Birch can be compared to trees of unnamed selections of *Betula pendula* known to the Inventor. Trees of the new Birch differ primarily from trees of unnamed selections of *Betula pendula* known to the Inventor in the following characteristics:

1. Trees of the new Birch are more dwarf than trees of unnamed selections of *Betula pendula.*
2. Trees of the new Birch are bushier than trees of unnamed selections of *Betula pendula.*
3. Trees of the new Birch do not produce flowers whereas trees of unnamed selections of *Betula pendula* produce flowers.

BRIEF DESCRIPTION OF THE PHOTOGRAPHS

The accompanying photographs illustrate the overall appearance of the new Birch tree showing the colors as true as it is reasonably possible to obtain in colored reproductions of this type. Colors in the photographs may differ slightly from the color values cited in the detailed botanical description which accurately describe the colors of the new Birch tree.

The photograph on the first sheet comprises a side perspective view of a typical tree of 'Globe' grown in an outdoor nursery.

The photograph on the second sheet comprises a close-up view of typical leaves of 'Globe'.

DETAILED BOTANICAL DESCRIPTION

The aforementioned photographs, following observations and measurements describe trees grown during the summer in Boskoop, The Netherlands in an outdoor nursery and under environmental conditions and cultural practices generally used in commercial Birch tree production. During the production of the trees, day temperatures ranged from 14° C. to 28° C. and night temperatures ranged from 8° C. to 16° C. Trees were four years old when the photographs and description were taken. In the following description, color references are made to The Royal Horticultural Society Colour Chart, 2007 Edition, except where general terms of ordinary dictionary significance are used.

Botanical classification: *Betula pendula* 'Globe'.

Parentage: Naturally-occurring branch mutation of *Betula pendula* 'Alba', not patented.

Tree description:

*Growth habit*.—Dwarf habit, globular in shape; dense and bushy; low vigor; freely branching habit, dense and bushy habit; about 53 main branches each with about twelve lateral branches.

*Height*.—About 70 cm.

*Diameter*.—About 70 cm.

*Branch description*.—Length, main branches: About 35.3 cm. Diameter, main branches: About 6 mm. Length, lateral branches: About 11.9 cm. Diameter, main branches: About 2 mm. Internode length: About 2 cm. Strength: Strong. Lenticels: Diameter: About 7.5 mm. Shape: Circular. Color: Close to 164B to 164C. Color, developing branches: Close to 144B. Color, developed branches: Upper surface, close to N199A; lower surface, close to 152A. Color, woody branches: Close to 199A.

*Leaf description*.—Arrangement: Alternate; simple. Length: About 5.2 cm. Width: About 3.5 cm. Shape: Broadly ovate. Apex: Acute to apiculate. Base: Acute. Margin: Serrate to dentate; undulate. Texture, upper and lower surfaces: Smooth, glabrous; somewhat leathery. Luster, upper and lower surfaces: Glossy. Venation pattern: Pinnate. Color: Developing leaves, upper surface: Close to 143B and 144A. Developing leaves, lower surface: Close to 143C. Fully expanded leaves, upper surface: Close to N137B; venation, close to 138B. Fully expanded leaves, lower surface: Close to 137C; venation, close to 144B. Petiole: Length: About 1.5 cm. Diameter: About 1 mm. Texture, upper and lower surfaces: Smooth, glabrous. Color, upper and lower surfaces: Close to 144B.

Flower description: Flower initiation and development has not been observed on trees of the new Birch.

Temperature tolerance: Trees of the new Birch have been observed to tolerate temperatures from about −20° C. to about 45° C.

Pathogen & pest resistance: Trees of the new Birch have not been observed to be resistant to pathogens or pests common to Birch trees.

It is claimed:

1. A new and distinct Birch tree named 'Globe' as illustrated and described.

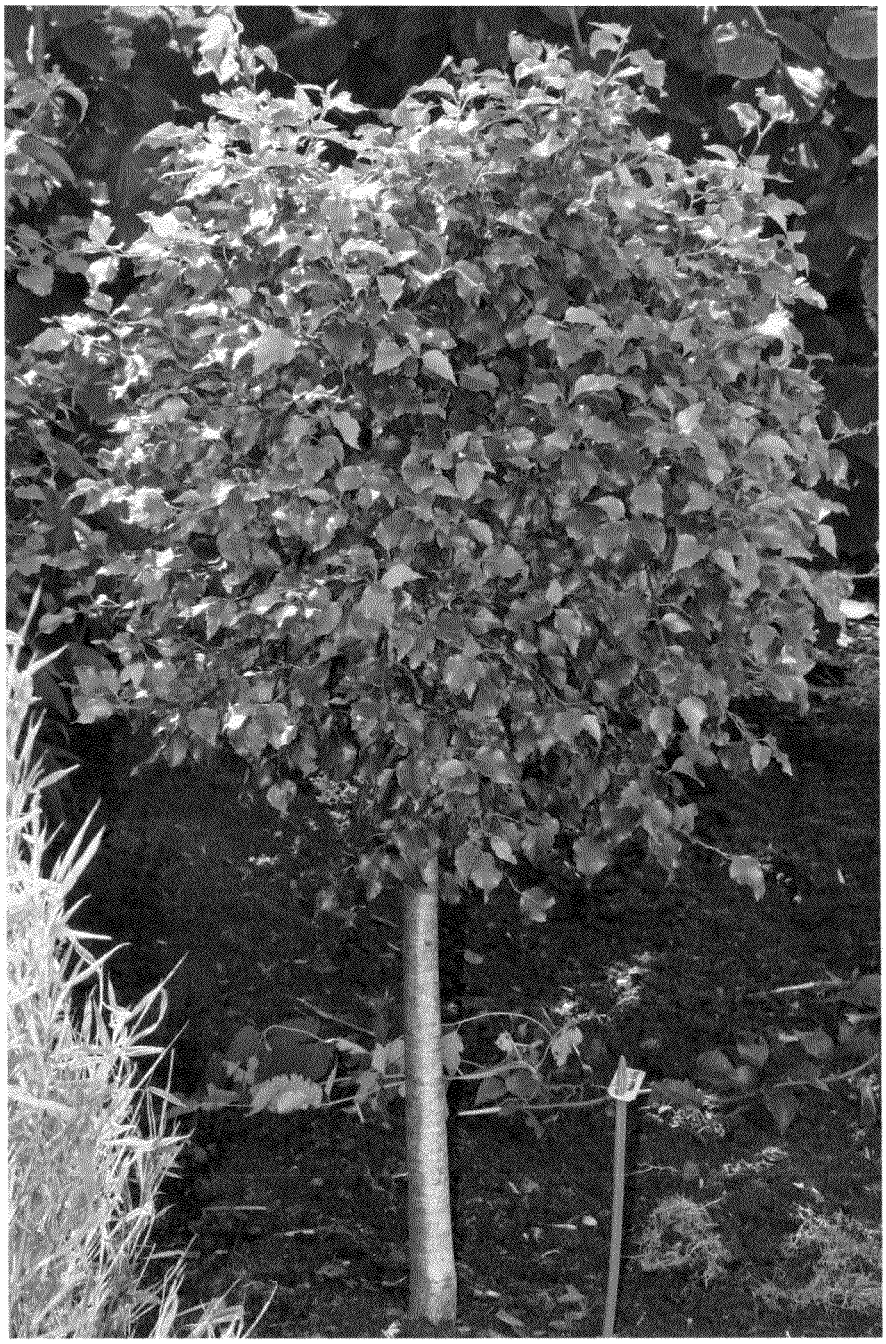

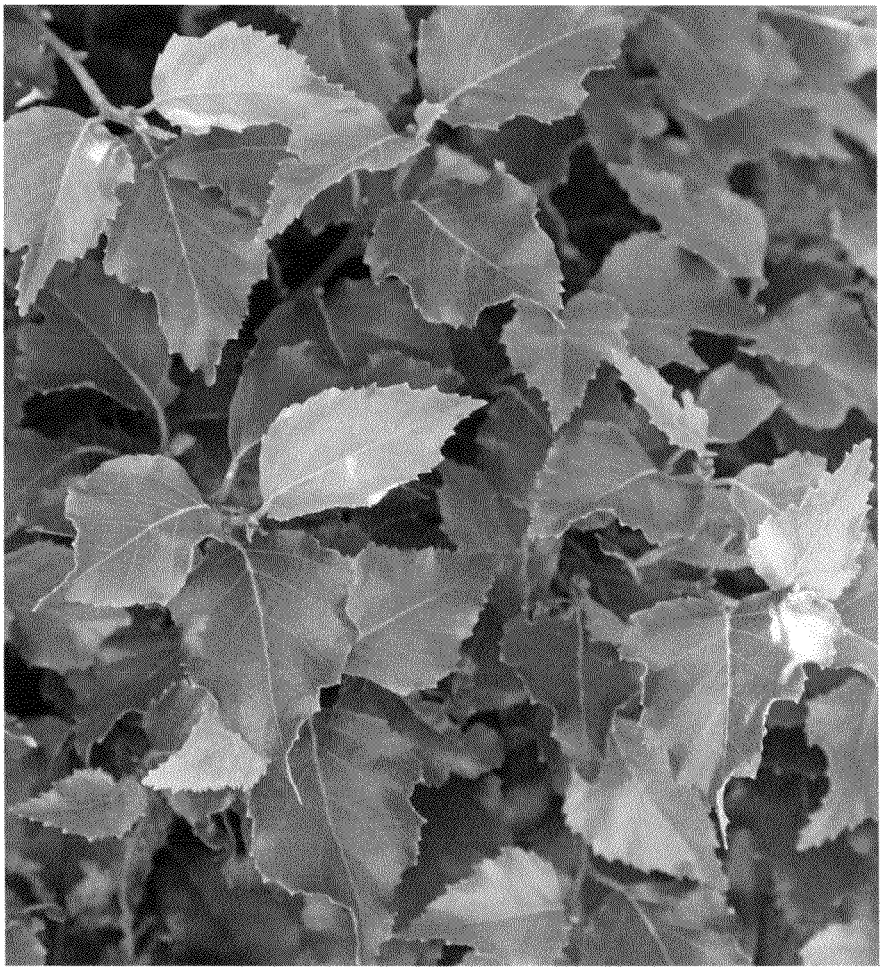

* * * * *